United States Patent [19]

Swartz et al.

[11] 4,183,499
[45] Jan. 15, 1980

[54] FLUID METERING VALVE

[76] Inventors: Delbert D. Swartz, 4808 Asteria St., Torrance, Calif. 90503; Masayuki Tamaya, 11232 Central Ave., South El Monte, Calif. 91733

[21] Appl. No.: 931,200

[22] Filed: Aug. 4, 1978

[51] Int. Cl.$^2$ ............................................. F16K 5/10
[52] U.S. Cl. .................................... 251/208; 251/352
[58] Field of Search ................ 251/208, 209, 352, 368

[56] References Cited

U.S. PATENT DOCUMENTS

| | | | |
|---|---|---|---|
| 2,832,562 | 4/1958 | Myers | 251/312 X |
| 3,048,192 | 8/1962 | Murphy, Jr. | 251/312 X |
| 3,214,069 | 10/1965 | Dike | 251/352 X |
| 3,292,898 | 12/1966 | Willman | 251/368 X |
| 3,323,774 | 6/1967 | Wilson | 251/352 X |
| 3,481,367 | 12/1969 | Deuschle | 251/368 X |
| 3,677,516 | 7/1972 | Hicks | 251/208 X |

*Primary Examiner*—Arnold Rosenthal
*Attorney, Agent, or Firm*—Singer & Singer

[57] ABSTRACT

A low pressure low volume plastic metering valve comprised of a cylinder having an external tapered port and a piston having a tapered through port for communicating with the port in said cylinder. Both the tapered port in the cylinder and the through port in the piston are offset from the axis of the cylinder and communicate with each other along an arcuate tapered passageway that varies from a maximum where the ports abut to a minimum. The piston is held by a lip on the cylinder walls which prevents axial movement of the piston but allows rotation of the piston to vary the fluid flow. Sealing is improved by constructing the cylinder of a yieldable plastic and the piston of a different plastic that is brittle and non-yielding.

8 Claims, 6 Drawing Figures

FLUID METERING VALVE

This invention relates to a low pressure low volume metering valve that is particularly adaptable to hospital environments where simple and accurate control of a metering of medicinal fluids is required.

In the art of metering valves for hospital use it is important to accurately control through a metering system a supply of fluids and medicines directly to the patient by means of intravenous feeding.

The art utilizes plastic tubes and spring-loaded pinching devices to restrict the flow of fluid through plastic tubes.

Devices of this type utilize soft yieldable plastic tubes that are deformable so as to restrict the passage of the fluid under control. Unfortunately, plastic suffers permanent deformation and it is almost impossible for the operator to change the flow rate on the tube after a set in the plastic has taken place.

Invariably the operator must remove the tube, attempt to push out the indentation, and if successful to repeat the pinching of the plastic until the desired flow rate is obtained. Invariably the tube that is deformed must be destroyed or removed and a new section of tube used that has not been subjected to any prior set or deformation.

At best, the control available by pinching the tube is haphazard, lacks accuracy, and is not reproducible from one position to another position, thereby making every initial control of fluid flow a new operation requiring much adjustment until the desired flow rate is obtained.

In the present invention there is disclosed a low pressure low volume fluid metering valve constructed completely of plastic and therefore acceptable for use in hospitals and other areas where contamination of the fluid medium by the valve mechanism is important.

The valve consists of two basic parts comprising a cylinder and a rotatable piston adapted to nest within the cylinder.

The cylinder contains a base member and wall portions and an external projecting tapered port member communicating with the interior of the cylinder through the base member.

The walls of the cylinder have a constant inside diameter near the base member and terminate with a lip having a camming surface which defines an enlarged internal diameter.

The rotatable piston nesting within the cylinder contains an upper disc and a lower disc that is restrained from moving in an axial direction by means of the lip on the wall portions of the cylinder contacting the upper disc on the piston. In this fashion the cylinder is rotatable but otherwise restrained from moving axially.

A tapered through port is located in the piston and is adapted to align with the port member in the base of the cylinder.

Both the port member in the cylinder and the through port in the piston are offset the same distance from the center of the cylinder.

In the preferred embodiment the bottommost portion of the piston contains an arcuate tapered passageway which provides an accurate control of fluid flow by rotating the piston in the direction of the arcuate taper.

Sealing between the cylinder and the piston is maintained by constructing the cylinder of a soft yieldable plastic whereas the piston is constructed of a brittle non-yielding plastic. The different plastic materials between the piston and the cylinder enhance the operation of the valve by eliminating sticking and thereby allowing a fine control to meter the flow of the fluid.

Assembly is enhanced since the external diameter of the lower disc is less than the internal diameter at the lip and hence the piston is insertable into the cylinder without affecting the sealing edge on the lower disc of the piston.

A review of the prior art shows that the use of an arcuate tapered passageway has been used to obtain a control of fluid flow. For example, U.S. Pat. No. 3,341,168 to Toeppen discloses a convoluted shaped opening for controlling the distribution of fluids.

Similarly, U.S. Pat. No. 1,751,591 to G. E. McCloskey and U.S. Pat. No. 1,191,700 to Howes also show the use of convoluted openings for controlling the flow of fluids.

Unfortunately the control valves shown in the prior art are complicated, requiring springs and seals that would prevent their use in a germ-free environment such as a hospital or other restricted area. In addition, the simplicity of the instant valve over the prior art is readily apparent by the elimination of O-rings and other seals by means of the unique construction disclosed and claimed.

Further objects and advantages of the present invention will be made more apparent by referring now to the accompanying drawings wherein.

Figure 1:
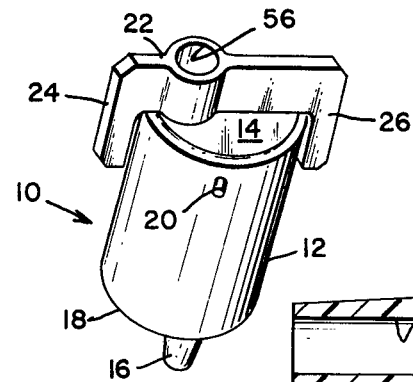
FIG. 1 is a perspective view of a plastic fluid metering valve constructed according to the present invention.

Referring now to FIG. 1, there is shown a perspective view of the complete metering valve 10 illustrating the cylinder portion 12 and the piston portion 14 located within the cylinder 12.

Located on the bottommost portion of the cylinder 12 is an external projecting tapered port member 16 communicating with the interior of the cylinder 12 through a base member 18.

A stub 20 attached to the outside of the cylinder 12 extends radially from the cylinder and is displaced a given number of degrees from the port member 16.

Attached to the uppermost portion of the piston 14 is a handle 22 having overlapping portions 24 and 26 that are each adapted to contact stub 20 when the piston 14 is rotated. Overlapping portion 24 contacting stub 20 will place the valve in a full opened position whereas overlapping portion 26 contacting the stub 20 will place the valve in an Off position.

Figure 2:
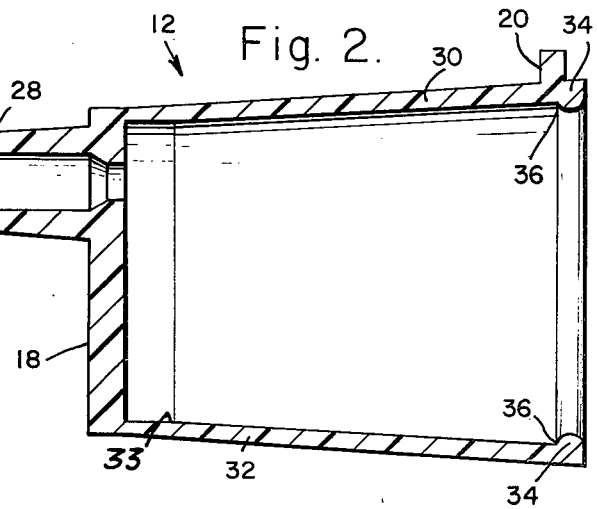
FIG. 2 is a cross-sectional view of the external cylinder portion of the metering valve.

Referring now to FIG. 2, there is shown a cross-sectional view of piston 12 more fully illustrating base member 18 and the external projecting tapered port member 16. A review of port 16 will show that the external surface is tapered whereas the internal surface 28 has a constant internal diameter.

The cylinder 12 is basically comprised of the base portion 18 and wall portions 30 and 32. In the preferred embodiment the external wall portions 30 and 32 are tapered in order to provide the necessary resiliency in the walls in the area of base member 18 to accept the piston 14 and to hold the piston in a rotatable engagement with the cylinder 12.

The internal wall portions 30 and 32 are substantially cylindrical in the area of the base member 18 so as to provide a constant internal diameter 33.

The internal diameter of the wall portions 30 and 32 extending from the constant inside diameter 33 are tapered and terminate in a lip 34 having a camming surface 36 located on the inside of the cylinder 12. The internal diameter of the lip 36 is larger than the constant internal diameter 33 located near the base member 18. Camming surface 36 is adapted to contact a similar surface on the piston 14 and to thereby hold the piston within the cylinder 12 and thereby prevent the piston from moving in an axial direction but otherwise allow the piston to be rotated.

Figure 3:
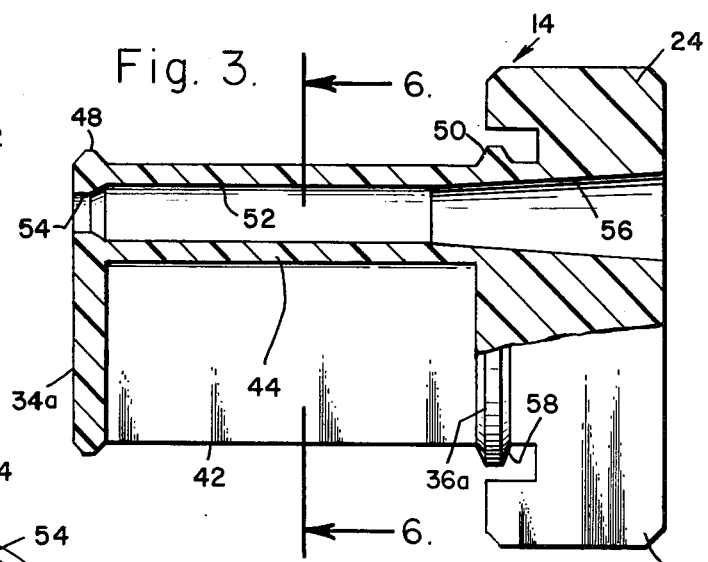
FIG. 3 is a cross-sectional view of the internal piston portion of the metering valve.

Referring now to FIG. 3, there is shown a cross-sectional view of the piston 14 which is constructed of the more brittle plastic that is non-yielding.

Figure 6:
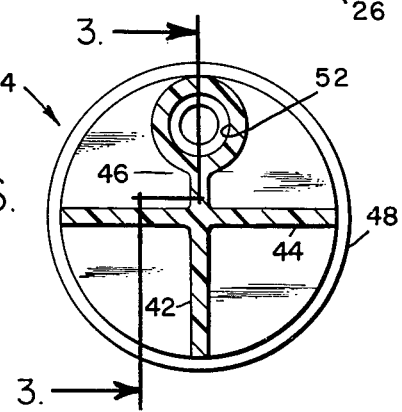
FIG. 6 is a cross-section taken along lines 6—6 of FIG. 3.

The piston 14 is constructed of a lower disc 34a and an upper disc 36a connected together by means of orthogonal vanes 40, 42, 44 and 46, more fully illustrated in connection with FIG. 6.

A pair of orthogonal vanes 40, 42, 44 and 46 are attached radially to the cylinder 38 and at each end to the lower disc 34a and the upper disc 36a thereby providing a rigid structure.

The outside diameter 48 of the lower disc 34 produces an interference fit with the internal diameter 33 of the cylinder, whereas the outside diameter 50 of the upper disc 36a is greater than the inside diameter of lip 34 thereby ensuring a close fit and good sealing action when the piston 14 is inserted within the cylinder 12.

In the preferred embodiment it is important that the sealing periphery comprised of diameter 48 on the lower disc 34a not be damaged during the insertion of the piston 14 into the cylinder 12. By having the internal diameter of lip 36 greater than the internal diameter 33, it is possible to insert the piston 14 into the cylinder without having the periphery of the lower disc 48 contact the lip 36.

The external diameter of the upper disc 50 is larger than the inside diameter of the lip 34 thereby ensuring that the camming surface 36 on the lip 34 will contact the camming surface 58 on the upper disc 36a to ensure that the piston is held in position after assembly.

Located within vane 46 is a port 52 that communicates with opening 54 in the lower disc 34 and a tapered opening 56 in the handle portion 22.

Located on the upper disc 36a is a camming surface 58 that is adapted to mate with the camming surface 36 on the lip 34 of the cylinder 12.

In operation the piston 14 is inserted into cylinder 12 and seated until bottommost portion of the lower disc 34a is in contact with the base member 18. In this position the camming surface 36 on the lip 34 will overlay and contact the camming surface 58 on the upper disc 36c. In this fashion the piston 14 will be held and prevented from moving in an axial direction while at the same time the piston will be allowed to rotate and held in an urging relationship into the cylinder 12 thereby improving the seal between the lower disc 14 and the base 18 of the cylinder 12.

Figure 4:
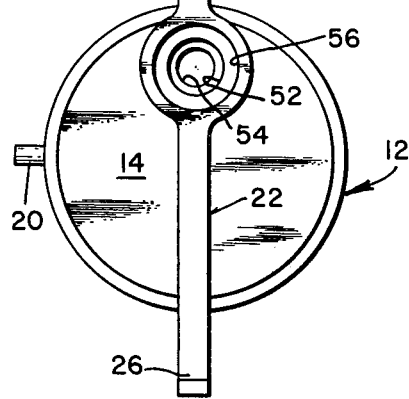
FIG. 4 is a top view of the piston portion of the metering valve.

Referring now to FIG. 4, there is shown a top view of the piston 14 more fully illustrating the handle 22 and the over-lapping portions 24 and 26. The tapered port 56 is located within the handle 22 and is adapted to receive a tube for supplying liquid to be needed.

Figure 5:
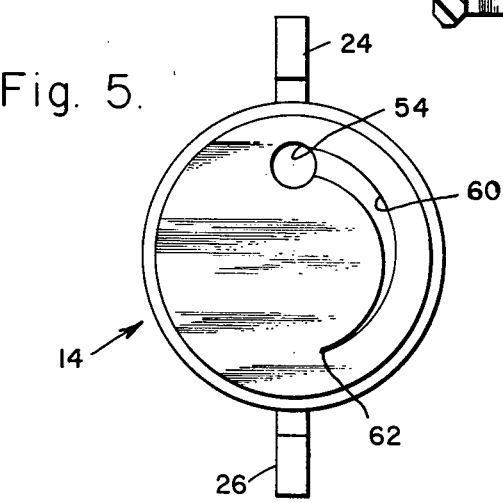
FIG. 5 is a bottom view of the piston portion of the metering valve.

Referring now to FIG. 5, there is shown a bottom view of the piston 14 more fully illustrating the preferred embodiment for metering the flow of liquid.

Located on the bottommost portion of the lower disc 34 is an arcuate tapered passageway 60 communicating at one end with port 54 and terminating at the other end 62. The arcuate passageway 60 is approximately 180 degrees from port 54 and is located on a constant radius measured from the center line of the piston 14.

In the practice of the present invention the arcuate passageway 60 may also be located on the internal surface of the base 60 and the same metering control of the liquid will be achieved by rotating the piston 14 relative to the cylinder 12.

In the preferred embodiment the valve is constructed of two different kinds of plastic with the cylinder 12 being constructed of nylon which is a more flexible yieldable plastic with a memory. A suitable nylon plastic presently available is sold under the name Zytel.

The piston portion 14 is preferably constructed of a hard plastic material that is non-yielding such as a polyacetate which is very brittle and not flexible. A suitable plastic is sold and available in the marketplace under the name Delrin.

Constructing the cylinder portion from a different plastic material than the piston portion prevents binding or sticking of the valve and facilitates obtaining an accurate metered flow of fluid.

Constructing the external wall portion 30 and 32 of the piston 12 in a tapered configuration provides a flexible wall near the base 18 and thereby provides an improved seal between the lowermost disc 34a of the piston 14.

We claim:

1. A fluid metering valve comprising:
    a tapered cylinder having walls and a base member,
    an external projecting tapered port member communicating with the interior of said cylinder through said base member, said cylinder having an inside diameter terminating with a lip having a camming surface defining an enlarged internal diameter,
    a rotatable piston adapted to nest within said cylinder and restrained by said lip from axial movement,
    said piston comprises a lower disc and an upper disc and in which the external diameter of the lower disc provides an interference fit with the internal diameter of said cylinder near said base member and in which the external diameter of the upper disc is larger than the internal diameter of said lip,
    a through port in said piston adapted to be aligned with said port member in said base member thereby providing a maximum flow rate,
    said port in said piston abutting with said port member in said cylinder along an arcuate tapered passageway whereby rotating said cylinder controls flow rate from a maximum to a minimum.

2. A valve according to claim 1 in which the internal diameter near the base member is cylidrical and a portion of the internal walls of said cylinder are tapered to provide a lip having an enlarged diameter.

3. A valve according to claim 1 in which said upper disc has a camming surface adapted to mate with the camming surface on said lip whereby the lip forces and holds the piston for rotational movement in the cylinder.

4. A valve according to claim 3 which includes a pair of interconnecting orthogonal vanes and interconnecting said upper and lower disc.

5. A valve according to claim 4 in which said through port is located in one of said vanes.

6. A valve according to claim 1 which includes a handle attached to said upper disc and in which said through port is tapered and extends through said handle.

7. A valve according to claim 6 which includes a radially projecting stub attached to the external side of said cylinder that is offset with respect to said port and in which said handle has overlapping sides projecting over said stub to stop handle rotation whereby the On and Off position of the valve is readily determined.

8. A valve according to claim 1 in which said cylinder is constructed of nylon plastic and said piston is constructed of polyacetate plastic.

* * * * *